United States Patent [19]

Lepage et al.

[11] Patent Number: 4,746,752
[45] Date of Patent: May 24, 1988

[54] PREPARATION OF HYDROGENOSILANES BY REDISTRIBUTION

[75] Inventors: Jean-Luc Lepage, Sainte-Foy-les-Lyon; Gerard Soula, Meyzieu, both of France

[73] Assignee: Rhone-Poulenc Specialites Chimiques, Courbevoie, France

[21] Appl. No.: 837,053

[22] Filed: Mar. 6, 1986

Related U.S. Application Data

[63] Continuation of Ser. No. 655,719, Sep. 28, 1984, abandoned.

[30] Foreign Application Priority Data

Sep. 28, 1983 [FR] France ............... 83 15403

[51] Int. Cl.$^4$ ............... C07F 7/08; C07F 7/18
[52] U.S. Cl. ............... 556/469
[58] Field of Search ............... 556/469

[56] References Cited

U.S. PATENT DOCUMENTS

| | | | |
|---|---|---|---|
| 2,834,648 | 5/1958 | Bailey et al. ............... | 556/469 X |
| 3,322,511 | 5/1967 | Weyenberg ............... | 556/469 X |
| 3,399,222 | 8/1968 | Weyenberg ............... | 556/469 |
| 3,445,200 | 5/1969 | Dunogues et al. ............... | 556/469 X |
| 3,465,019 | 9/1969 | Berger ............... | 556/469 X |

FOREIGN PATENT DOCUMENTS

| | | | |
|---|---|---|---|
| 0253653 | 2/1967 | Canada ............... | 556/469 |
| 1444735 | 5/1966 | France ............... | 556/469 |
| 2096605 | 2/1972 | France ............... | 556/469 UX |

*Primary Examiner*—Paul F. Shaver
*Attorney, Agent, or Firm*—Burns, Doane, Swecker & Mathis

[57] ABSTRACT

Hydrogenated silanes are facilely prepared by redistribution, by reacting (1) a silane having the formula $H_mSiX_{4-m}$ in which X is halogen or an alkoxy group and m is an integer equal to 0, 1, 2 or 3, with (2) an alkyl or aryl hydrosilane having the formula $R_nH_pSiX'_{4-(n+p)}$ in which X' is halogen or an alkoxy group, R is an alkyl or aryl group and n and p, which may be identical or different, are integers equal to 1, 2 or 3, with the proviso that $n+p \leq 4$, in the presence of (3) a catalytically effective amount of a catalyst comprising (i) a quaternary ammonium salt having the formula $R'_4NY$ or a quaternary phosphonium salt having the formula $R'_4PY$, in which formulae R', which may be identical or different, are each a monovalent hydrocarbon radical and Y is halogen, (ii) a tertiary amine of the general formula NR'R''R''', in which R', R'' and R''', which may be identical or different, are monovalent hydrocarbon radicals, or (iii) an ion exchange resin comprising tertiary amine or quaternary ammonium groups.

9 Claims, No Drawings

PREPARATION OF HYDROGENOSILANES BY REDISTRIBUTION

This application is a continuation of Ser. No. 06/665,719, filed Sept. 28, 1984, now abandoned.

BACKGROUND OF THE INVENTION

1. Field of the Invention

The present invention relates to the preparation of hydrogenated silanes by redistribution, and, more especially, to the preparation of a silane containing at least one Si—H bond by reacting a less hydrogenated or non-hydrogenated silane with an alkyl or aryl hydrosilane in the presence of a catalyst.

2. Description of the Prior Art

It is known to this art to prepare silanes containing at least two Si—H bonds by disproportionation of two hydrosilane molecules containing alkyl or aryl groups, if appropriate. Thus, French Pat. Nos. 2,096,605, 2,118,725, 2,261,977, 2,290,447, and 2,290,448 describe such disproportionation reactions in the presence of various catalysts, wherein such disproportionation reactions can be represented as follows:

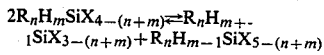

$$2R_nH_mSiX_{4-(n+m)} \rightleftharpoons R_nH_{m+1}SiX_{3-(n+m)} + R_nH_{m-1}SiX_{5-(n+m)}$$

in which n denotes an integer equal to 0, 1 or 2; m denotes an integer equal to 1, 2 or 3 with $n+m \leq 3$, and R denotes an alkyl or aryl group and X a halogen.

It is also known to prepare alkyl or aryl hydrosilanes by redistribution between a molecule of hydrosilane and a molecule of alkyl or aryl halosilane. The described catalysts for these redistribution reactions are notably those which are the subject of French Pat. Nos. 1,603,167, 2,290,447, 2,467,855, 2,290,448, 2,096,605 and 2,119,477, wherein such redistribution reactions can be represented as follows:

$$H_mSiX_{4-m} + R_nSiX_{4-n} \rightarrow H_{m-1}SiX_{5-m} + R_nHSiX_{3-n}$$

in which m denotes an integer equal to 1, 2, 3 or 4 and n denotes an integer equal to 1, 2 or 3 and R denotes an alkyl or aryl group and X a halogen.

SUMMARY OF THE INVENTION

A major object of the present invention is the provision of an improved process for the preparation of a hydrogenated silane by a novel redistribution reaction between a silane which is less hydrogenated than that sought to be produced or is non-hydrogenated, and an alkyl or aryl hydrosilane, in the presence of a catalytic system, and wherein such reaction can be represented as follows:

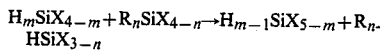

$$H_mSiX_{4-m} + R_nH_pSiX'_{4-(n+p)} \rightarrow H_{m+1}SiX_{3-m} + R_nH_{p-1}SiX'_{4-(n+p)}X$$

in which R denotes an alkyl or aryl group, X and X', which may be identical or different, denote a halogen or an alkoxy group, m denotes an integer equal to 0, 1, 2 or 3; n and p, which may be identical or different, denote integers equal to 1, 2 or 3 with $n+p \leq 4$.

The improved process according to this invention makes it possible to prepare hydrosilanes which are more fully hydrogenated than the beginning or starting material silane, with conversions which are much higher than those obtained when such desired final products are produced by disproportionation; it moreover makes it possible to valorize byproducts obtained during the direct synthesis of methyl chlorosilanes, such as methyldichlorosilane. Further, the process according to the invention is particularly suitable for the preparation of trichlorosilane, dichlorosilane and/or silane according to the reactions:

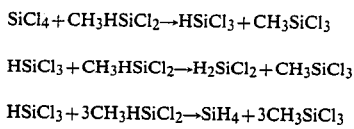

$$SiCl_4 + CH_3HSiCl_2 \rightarrow HSiCl_3 + CH_3SiCl_3$$

$$HSiCl_3 + CH_3HSiCl_2 \rightarrow H_2SiCl_2 + CH_3SiCl_3$$

$$HSiCl_3 + 3CH_3HSiCl_2 \rightarrow SiH_4 + 3CH_3SiCl_3$$

The process according to the invention thus also makes it possible to produce raw materials which permit easy access to silicon of photovoltaic or electronic quality. It also permits the valorization of tetrachlorosilane, a byproduct of the manufacture of silicon of photovoltaic or electronic quality, by cracking trichlorosilane. Tetrachlorosilane is thus valorized by conversion to trichlorosilane and/or dichlorosilane under conditions which are notably economical when compared to those known from the literature.

Briefly, the present invention features a process for the preparation of hydrogenated silane via redistribution, by reacting (1) a silane having the formula $H_mSiX_{4-m}$ in which X denotes a halogen or an alkoxy group and m denotes an integer equal to 0, 1, 2 or 3, with (2) an alkyl or aryl hydrosilane having the formula $R_nH_pSiX'_{4-(n+p)}$ in which X' denotes a halogen or an alkoxy group, R denotes an alkyl or aryl group and n and p, which may be identical or different, denote integers equal to 1, 2 or 3 with $n+p \leq 4$; in the presence of (3) a catalyst selected from among (i) quaternary ammonium salts having the formula $R'_4NY$, quaternary phosphonium salts having the formula $R'_4PY$, in which formulae R', which may be identical or different, denote a monovalent hydrocarbon radical and Y a halogen; (ii) tertiary amines of the general formula $NR'R''R'''$, in which R', R'', R''' are monovalent hydrocarbon radicals which may be identical or different; (iii) ion exchange resins containing tertiary amine groups or quaternary ammonium groups; and thereafter recovering the hydrogenated silane or silanes formed.

DETAILED DESCRIPTION OF THE INVENTION

More particularly according to the present invention, the silanes which are used are preferably those having the formula $H_mSiX_{4-m}$ in which X denotes a halogen or alkoxy group and m an integer equal to 0, 1, 2 or 3. In a preferred embodiment of the invention, tetrachlorosilane, trichlorosilane, dichlorosilane, or admixture thereof, are used.

The alkyl or aryl hydrosilanes which are employed in the process of the invention are those which have the formula $R_nH_pSiX'_{4-(n+p)}$ in which X' denotes a halogen or an alkoxy group, R denotes an alkyl or aryl group and n and p, which may be identical or different, denote integers equal to 1, 2 or 3 with $n+p \leq 4$.

In another preferred embodiment of the invention, methylsilane, methylchlorosilane, dimethylchlorosilane, methyldichlorosilane, dimethylsilane, trimethylsilane, phenyldichlorosilane, phenylchlorosilane, diphenylchlorosilane, ethyldichlorosilane, or admixtures thereof, are used.

The quaternary ammonium salts employed consistent with this invention correspond to the formula $R'_4NY$ and the quaternary phosphonium salts employed according to the invention correspond to the formula $R'_4PY$, in which formulae $R'$, which may be identical or different, denote a monovalent hydrocarbon radical and Y a halogen.

Preferably, $R'$ may be any monovalent hydrocarbon radical, for example, one of the alkyl radicals, such as a methyl, ethyl, isopropyl, butyl, secondary hexyl, 2-ethylhexyl or octadecyl radical, one of the cycloalkyl radicals, such as a cyclohexyl or cyclopentyl radical, one of the aliphatically unsaturated radicals, such as a vinyl, allyl, hexenyl, cyclopentenyl or butadienyl radical, or one of the radicals containing aryl groups, such as a phenyl, tolyl, benzyl, diphenyl, or naphthyl radical.

$R'$ may also be any monovalent halohydrocarbon radical, for example, one of the haloalkyl radicals, such as a 3-chloropropyl, 3,3,3-trifluoropropyl or 4-bromohexyl radical, a halocycloalkyl radical, such as a bromocyclopentyl or difluorocyclohexyl radical, one of the aliphatically unsaturated radicals, such as a chloroallyl or chlorocyclohexenyl radical, and one of the radicals containing aryl groups, such as a chlorophenyl, dibromophenyl, $\alpha,\alpha,\alpha$-trifluorotolyl or bromonaphthyl radical.

Y may be any halogen, for example, chlorine, bromine or iodine.

The tertiary amines employed according to the invention correspond to the general formula $NR'R''R'''$ in which $R'$, $R''$ and $R'''$ are monovalent hydrocarbon radicals which may be identical or different.

Preferably, $R'$, $R''$, $R'''$ may be any alkyl, aryl, cycloalkyl, alkylaryl, alkylcycloalkyl, alkenyl, or alkylene (when $R'$ and $R''$ are joined together) radical; in general, these radicals have a total number of carbon atoms which is less than 22.

The tertiary amines which are most commonly employed are particularly the following: tri-n-propylamine, triisopropylamine, diisopropylethylamine, tri-n-butylamine, triisobutylamine, tri-sec-butylamine, tri-n-pentylamine, di-n-butylethylamine, diisobutylethylamine, di-2-ethylbutylmethylamine, di-n-octylmethylamine, di-2-ethylhexylmethylamine, dilaurylmethylamine, triundecylamine, trioctadecylamine, n-octadecyl-n-propylethylamine, di-n-butylphenylamine, triphenylamine, tris-(diphenyl)amine, 2-naphthyldi-n-butylamine, tritolylamine, trixylylamine, tris(phenylmethylphenyl)amine, tris(2-phenylethyl)amine, tris(8-phenyloctyl)amine, tricyclohexylamine, tricyclooctylamine, tris(4-methylcyclohexyl)amine, tris(2-cyclohexylethyl)amine, tris(3-n-butenyl)amine, triisobutenylamine, diallyl-n-butylamine, N-n-propylpiperidine, N-isobutylpyrrolidine, N-isobutylmorpholine, and the like.

The catalyst used in the process of the invention may also comprise an ion exchange resin which is insoluble in the reagents employed in the reaction and incorporating tertiary amine groups or quaternary ammonium groups in which the alkylamine or alkylammonium radicals preferably contain from 1 to 8 carbon atoms, such groups being joined via a carbon atom to the resin structure.

The process according to the invention may be carried out in the presence or in the absence of a solvent. In the latter case, the original silanes may act as a solvent. When a third solvent is employed, the latter must meet a number of conditions: it must dissolve the starting material silanes; it must also be chemically inert vis-a-vis the silanes which are introduced or formed.

Preferably, a solvent is selected such as, for example, chlorobenzene, orthodichlorobenzene, benzene, toluene, cyclohexane, heptane, dichloroethane, methylene chloride, dichlorobenzene, tetrahydrofuran, dioxane, or dimethoxyethane.

The process according to the invention is advantageously carried out at a temperature ranging from $-30°$ C. to the boiling point of the reaction medium.

Preferably, the reaction is carried out at atmospheric pressure. Pressures above or below atmospheric pressure are not, of course, excluded.

The catalyst is employed in an amount such that the molar ratio of the catalyst (or, in the case of the resins, of the active groups in the resin) to the starting material silanes (silane and alkyl or aryl hydrosilane) preferably ranges from 10 to 0.0001. More preferably, it ranges from 0.5 to 0.005.

The molar ratio between the silane and the alkyl or aryl hydrosilane preferably ranges from 0.1 to 5. When this ratio is high, the reaction is restricted to the formation of silanes having a low degree of hydrogenation; on the other hand, when this ratio is low, the reaction may be continued until more highly hydrogenated silanes are formed, up to $SiH_4$.

The molar ratio of the solvent to the starting material silanes advantageously ranges from 0 to 100 and preferably from 0 to 10.

The hydrosilane or hydrosilanes may be separated as they are formed, when they are poorly soluble in the reaction medium and sufficiently volatile. It is also possible to separate, upon completion of the reaction, the various silanes produced (the hydrosilane or hydrosilanes and the alkyl or aryl silane or silanes formed) and the unreacted silanes, using methods which are well known to this art, such as, for example, distillation, selective solubilization, and the like.

It will be appreciated that the catalyst system employed according to the invention also catalyzes at the same time the disproportionation reactions of the silanes containing at least one Si—H bond; thus, the redistribution reaction immediately above described, followed by simultaneous disproportionation reactions of the silanes which are present and containing at least one Si—H bond may lead to the production of more or less complex mixtures of silanes. For example, the redistribution reaction may be overall represented as follows:

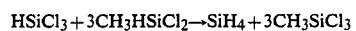

and in fact corresponds to the sum of the redistribution reaction

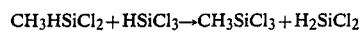

and the disproportionation reaction $3H_2SiCl_2 \rightarrow SiH_4 + 2HSiCl_3$. In the case where the silane employed for the redistribution reaction is tetrachlorosilane, which does not disproportionate (it does not contain Si—H bonds), if it is desired to avoid the disproportionation of the $H_2SiCl_2$ formed by the redistribution reaction, it should be recovered as it is being formed.

The present invention thus makes it possible to prepare hydrogenated silanes according to a novel redistribution reaction with an outstanding conversion and, in general, employing but small amounts of catalyst.

In order to further illustrate the present invention and the advantages thereof, the following specific examples are given, it being understood that same are intended only as illustrative and in nowise limitative.

EXAMPLE 1

Into an 8-ml flask fitted with a Viton ® septum were introduced:

(i) $28.5 \ 10^{-3}$ moles of chlorobenzene (solvent), i.e., 3.209 g, (ii) $0.39 \ 10^{-3}$ moles of tetrabutylammonium chloride, i.e., 108.3 mg.

After the flask had been heated to a temperature of 30° C., (iii) $8.78 \ 10^{-3}$ moles of $CH_3SiHCl_2$, i.e., 1.010 g, and (iv) $4.67 \ 10^{-3}$ moles of $HSiCl_3$, i.e., 0.633 g, were introduced with the aid of a syringe. The redistribution reaction between $CH_3SiHCl_2$ and $HSiCl_3$ was followed by periodic analyses of the reaction medium using gas phase chromatography.

After 5 hours of reaction, the reaction composition was as follows (weight percentages):

| (1) $SiH_4$ | 0.14% |
|---|---|
| (2) $H_3SiCl$ | 0.52% |
| (3) $CH_3SiH_2Cl$ | 0.19% |
| (4) $H_2SiCl_2$ | 3.81% |
| (5) $HSiCl_3$ | 5.90% |
| (6) $CH_3SiHCl_2$ | 12.20% |
| (7) $SiCl_4$ | 0.10% |
| (8) $CH_3SiCl_3$ | 10.25% |
| (9) $C_6H_5Cl$ | 64.70% | which corresponds to a $HSiCl_3$ conversion of 54% and a $CH_3SiHCl_2$ conversion of 40%.

It will be appreciated that the reaction between $HSiCl_3$ and $CH_3SiHCl_2$ was followed by a reaction of the same type between $H_2SiCl_2$ formed and $CH_3SiHCl_2$, with formation of $H_3SiCl$ and of $SiH_4$. To these reactions may be added those of disproportionation of the various silanes present in the reaction medium, these reactions being catalyzed by the same catalyst systems.

The main reaction, followed by the reactions mentioned immediately above, can therefore lead to the production of more or less complex mixtures of silanes.

EXAMPLE 2

In this example the procedure of Example 1 was repeated, but with the solvent $C_6H_5Cl$ being replaced with cyclohexane:

| (i) Cyclohexane | 2.184 g | ($25.9 \ 10^{-3}$ moles) |
|---|---|---|
| (ii) $(C_4H_9)_4NCl$ | 131.8 mg | ($0.47 \ 10^{-3}$ moles) |
| (iii) $HSiCl_3$ | 0.558 g | ($4.12 \ 10^{-3}$ moles) |
| (iv) $CH_3SiHCl_2$ | 0.909 g | ($7.90 \ 10^{-3}$ moles) |

After 20 hours of reaction, the reaction composition was as follows:

| (1) $SiH_4$ | 0.17% |
|---|---|
| (2) $H_3SiCl$ | 0.53% |
| (3) $CH_3SiH_2Cl$ | 0.19% |
| (4) $H_2SiCl_2$ | 4.17% |
| (5) $HSiCl_3$ | 7.13% |
| (6) $CH_3SiHCl_2$ | 15.30% |
| (7) $SiCl_4$ | 0.31% |
| (8) $CH_3SiCl_3$ | 10.99% |
| (9) $C_6H_{12}$ | 57.73% |

This corresponds to a conversion of $HSiCl_3$ of 52% and a conversion of $CH_3SiHCl_2$ of 36%.

EXAMPLE 3

In this example, a redistribution between $HSiCl_3$ and $CH_3SiHCl_2$ was tested, still in the presence of $(C_4H_9)_4NCl$, but without a solvent:

| (i) $(C_4H_9)_4NCl$ | 137.4 mg | ($0.49 \ 10^{-3}$ moles) |
|---|---|---|
| (ii) $HSiCl_3$ | 0.440 g | ($3.35 \ 10^{-3}$ moles) |
| (iii) $CH_3SiHCl_2$ | 0.970 g | ($8.43 \ 10^{-3}$ moles) |

After 1 hour, 20 min of reaction, the reaction composition was as follows:

| (1) $SiH_4$ | 0.21% |
|---|---|
| (2) $H_3SiCl$ | 0.65% |
| (3) $CH_3SiH_2Cl$ | 0.52% |
| (4) $H_2SiCl_2$ | 10.12% |
| (5) $HSiCl_3$ | 11.99% |
| (6) $CH_3SiHCl_2$ | 45.79% |
| (7) $SiCl_4$ | 0.88% |
| (8) $CH_3SiCl_3$ | 20.96% | which corresponds to a conversion of $HSiCl_3$ of 58% and a conversion of $CH_3SiHCl_2$ of 27%.

EXAMPLE 4

In this example the procedure of Example 1 was repeated, but replacing $(C_4H_9)_4NCl$ with tetrabutylphosphonium chloride $(C_6H_9)_4PCl$.

| (i) Chlorobenzene | 3.173 g | ($28.2 \ 10^{-3}$ moles) |
|---|---|---|
| (ii) $(C_4H_9)_4PCl$ | 149.6 mg | ($0.51 \ 10^{-3}$ moles) |
| (iii) $HSiCl_3$ | 0.684 g | ($5.05 \ 10^{-3}$ moles) |
| (iv) $CH_3SiHCl_2$ | 1.006 g | ($8.75 \ 10^{-3}$ moles) |

After 5 hours of reaction, the reaction composition was as follows:

| (1) $SiH_4$ | 0.18% |
|---|---|
| (2) $H_3SiCl$ | 0.80% |
| (3) $CH_3SiH_2Cl$ | 0.23% |
| (4) $H_2SiCl_2$ | 3.95% |
| (5) $HSiCl_3$ | 5.84% |
| (6) $CH_3SiHCl_2$ | 10.37% |
| (7) $SiCl_4$ | 0.17% |
| (8) $CH_3SiCl_3$ | 12.20% |
| (9) $C_6H_5Cl$ | 63.29% | which corresponds to a conversion of $HSiCl_3$ of 57% and a conversion of $CH_3SiHCl_2$ of 53%.

EXAMPLE 5

The above procedure was repeated, but using $(C_4H_9)_3N$ as the catalyst, again in the presence of $C_6H_5Cl$ as a solvent.

| (i) Chlorobenzene | 3.058 g | ($27.2 \ 10^{-3}$ moles) |
|---|---|---|
| (ii) $(C_4H_9)_3N$ | 89.8 mg | ($0.48 \ 10^{-3}$ moles) |
| (iii) $HSiCl_3$ | 0.530 g | ($3.91 \ 10^{-3}$ moles) |
| (iv) $CH_3SiHCl_2$ | 0.994 g | ($8.64 \ 10^{-3}$ moles) |

After 24 hours of reaction, the reaction composition was as follows:

| (1) SiH$_4$ | 0% |
|---|---|
| (2) H$_3$SiCl | 0.11% |
| (3) CH$_3$SiH$_2$Cl | 0.09% |
| (4) H$_2$SiCl$_2$ | 2.03% |
| (5) HSiCl$_3$ | 8.03% |
| (6) CH$_3$SiHCl$_2$ | 18.62% |
| (7) SiCl$_4$ | 0.44% |
| (8) CH$_3$SiCl$_3$ | 3.30% |
| (9) C$_6$H$_5$Cl | 65.46% | which corresponds to a conversion of HSiCl$_3$ of 29% and a conversion of CH$_3$SiHCl$_2$ of 13%.

EXAMPLE 6

In this example, redistribution between HSiCl$_3$ and CH$_3$SiHCl$_2$ was tested, using Amberlyst A 21 ® as the catalyst, without any solvent.

Amberlyst A 21 ® is an anion exchange resin, weakly basic, containing the active groups —N(CH$_3$)$_2$.

Before using the catalyst, it was dried by azeotropic removal of water using hexane, followed by removal of the residual solvent by drying under vacuum at 60° C.

The test was carried out on the following reaction mixture:

| (i) Amberlyst A 21 ® (dried) | 124.5 mg | |
|---|---|---|
| (ii) HSiCl$_3$ | 1.569 g | (11.58 10$^{-3}$ moles) |
| (iii) CH$_3$SiHCl$_2$ | 2.253 g | (19.59 10$^{-3}$ moles) |

After 24 hours of reaction, the reaction composition was as follows:

| (1) SiH$_4$ | 0.05% |
|---|---|
| (2) H$_3$SiCl | 0.37% |
| (3) CH$_3$SiH$_2$Cl | 0.29% |
| (4) H$_2$SiCl$_2$ | 8.55% |
| (5) HSiCl$_3$ | 25.90% |
| (6) CH$_3$SiHCl$_2$ | 45.96% |
| (7) SiCl$_4$ | 1.81% |
| (8) CH$_3$SiCl$_3$ | 13.94% | which corresponds to a conversion of HSiCl$_3$ of 35% and a conversion of CH$_3$SiHCl$_2$ of 19%.

EXAMPLE 7

In this example the procedure of Example 6 was repeated, but replacing Amberlyst A 21 ® with Amberlyst A 26 ®.

Amberlyst A 26 ® is an anion exchange resin, strongly basic, containing the active groups —N(CH$_3$)$_3$Cl.

Same was dried before use under the same conditions as above for the Amberlyst A 21 ®.

The test was carried out on the following reaction mixture:

| (i) Amberlyst A 26 ® (dried) | 117.6 g | |
|---|---|---|
| (ii) HSiCl$_3$ | 0.699 g | (5.16 10$^{-3}$ moles) |
| (iii) CH$_3$SiHCl$_2$ | 1.097 g | (9.54 10$^{-3}$ moles) |

After 20 hours of reaction, the reaction composition was as follows:

| (1) SiH$_4$ | 0.02% |
|---|---|
| (2) H$_3$SiCl | 0.28% |
| (3) CH$_3$SiH$_2$Cl | 0.17% |
| (4) H$_2$SiCl$_2$ | 7.18% |
| (5) HSiCl$_3$ | 24.20% |
| (6) CH$_3$SiHCl | 49.28% |
| (7) SiCl$_4$ | 2.57% |
| (8) CH$_3$SiCl$_3$ | 10.15% | which corresponds to a conversion of HSiCl$_3$ of 34% and a conversion of CH$_3$SiHCl$_2$ of 14%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of hydrogenated silane, comprising redistributing (1) a silane having the formula H$_m$SiX$_{4-m}$ in which X is halogen or an alkoxy group and m is an integer equal to 0, 1, 2 or 3, by reacting said silane with (2) an alkyl or aryl hydrosilane having the formula R$_n$H$_p$SiX'$_{4-(n+p)}$ in which X' is halogen or an alkoxy group, R is an alkoxy or aryl group and n and p, which may be identical or different, are integers equal to 1, 2 or 3, with the proviso that n+p≦4, in the presence of (3) a catalytically effective amount of a catalyst comprising (i) a quaternary ammonium salt having the formula R'$_4$NY or a quaternary phosphonium salt having the formula R'$_4$PY, in which formulae R', which may be identical or different, are each a monovalent hydrocarbon radical and Y is halogen, (ii) a tertiary amine of the general formula NR'R"R"', in which R', R" and R"', which may be identical or different, are monovalent hydrocarbon radicals, or (iii) an ion exchange resin comprising tertiary amine or quaternary ammonium groups.

2. The process as defined by claim 1, carried out in the presence of a catalyst (i), wherein R' is methyl, ethyl, isopropyl, butyl, secondary hexyl, 2-ethylhexyl, octadecyl, cyclohexyl, cyclopentyl, vinyl, allyl, hexenyl, cyclopentenyl, butadienyl, phenyl, tolyl, benzyl, diphenyl, naphthyl, 3-chloropropyl, 3,3,3-trifluoropropyl, 4-bromohexyl, bromocyclopentyl, difluorocyclohexyl, chloroallyl, chlorocyclohexenyl, chlorophenyl, dibromophenyl, α,α,α-trifluorotolyl, or bromonaphthyl.

3. The process as defined by claim 1, carried out in the presence of a catalyst (ii) comprising tri-n-propylamine, triisopropylamine, diisopropylethylamine, tri-n-butylamine, triisobutylamine, tri-sec-butylamine, tri-n-pentylamine, di-n-butylethylamine, diisobutylethylamine, di-2-ethylbutylmethylamine, di-n-octylmethylamine, di-2-ethylhexylmethylamine, dilaurylmethylamine, tri-undecylamine, trioctadecylamine, n-octadecyl-n-propyl-ethylamine, di-n-butylphenylamine, triphenylamine, tris(diphenyl)amine, 2-naphthyldi-n-butylamine, tritolylamine, trixylylamine, tris(phenylmethylphenyl)amine, tris(2-phenylethyl)amine, tris(8-phenyloctyl)amine, tricyclohexylamine, tricyclooctylamine, tris(4-methylcyclohexyl)amine, tris(2-cyclohexylethyl)amine, tris(3-n-butenyl)amine, triisobutenylamine, diallyl-n-butylamine, N-n-propylpiperidine, N-isobutylpyrrolidine, or N-isobutylmorpholine.

4. The process as defined by claim 1, carried out in the presence of a catalyst (iii) wherein the ion exchange resin is insoluble in the reagents employed in the reaction and comprising tertiary alkylamine or quaternary alkylammonium groups, the alkyl radicals of which having from 1 to 8 carbon atoms.

5. The process as defined by claim 1, wherein the molar ratio of catalyst to the starting material silanes ranges from 10 to 0.0001.

6. The process as defined by claim 5, said ratio ranging from 0.5 to 0.005.

7. The process as defined by claim 5, said silane (1) comprising tetrachlorosilane, trichlorosilane, dichlorosilane, or admixture thereof.

8. The process as defined by claim 7, said hydrosilane (2) comprising methylsilane, methylchlorosilane, dimethylchlorosilane, methyldichlorosilane, dimethylsilane, trimethylsilane, phenyldichlorosilane, phenylchlorosilane, diphenylchlorosilane, ethyldichlorosilane, or admixture thereof.

9. The process as defined by claim 1, carried out in the presence of a reaction solvent.

* * * * *